United States Patent [19]

Plourde

[11] Patent Number: 4,461,368
[45] Date of Patent: Jul. 24, 1984

[54] DIAPHRAGM COVER FOR A STETHOSCOPE

[76] Inventor: R. Gilles Plourde, 5025 MacDonald Ave., #104, Montreal, Quebec, Canada, H3X-2V2

[21] Appl. No.: 368,749

[22] Filed: Apr. 15, 1982

[51] Int. Cl.³ .............................. A61B 5/02; A61B 7/02
[52] U.S. Cl. ........................................ 181/131; 181/137
[58] Field of Search ....................... 181/126, 131, 137; 179/184, 185, 1 ST

[56] References Cited

U.S. PATENT DOCUMENTS

| 2,651,380 | 9/1953 | Brandenburg | 181/137 |
| 3,255,841 | 6/1966 | Hasbrouck | 181/126 |
| 3,867,925 | 2/1975 | Ersek | 181/131 X |

OTHER PUBLICATIONS

Mangi et al., "Contaminated Stethoscopes: A Potential Source of Nosocomial Injections", Yale Journal of Biology and Medicine, 45,600-45,604 (1972).

Primary Examiner—L. T. Hix
Assistant Examiner—Douglas S. Lee
Attorney, Agent, or Firm—Marvin E. Jacobs

[57] ABSTRACT

The surface of a diaphragm 26 is maintained in hygienic condition during examination of successive patients by positioning a clean or sterile diaphragm cover 10 over the diaphragm during examination. The cover 10 can be disposed or resterilized for further use. The cover 10 includes a flexible, resilient, imperforate membrane sheet 32 mounted on a rigid rim member 30 containing at least one, and preferably two, tabs 34 which clip over the outer edge of the ring 26. The rim of the cover is designed to have a loose sliding fit over the cup and the cover sheet is very thin and deformable so that there is no interference with sound collection and transmission.

5 Claims, 4 Drawing Figures

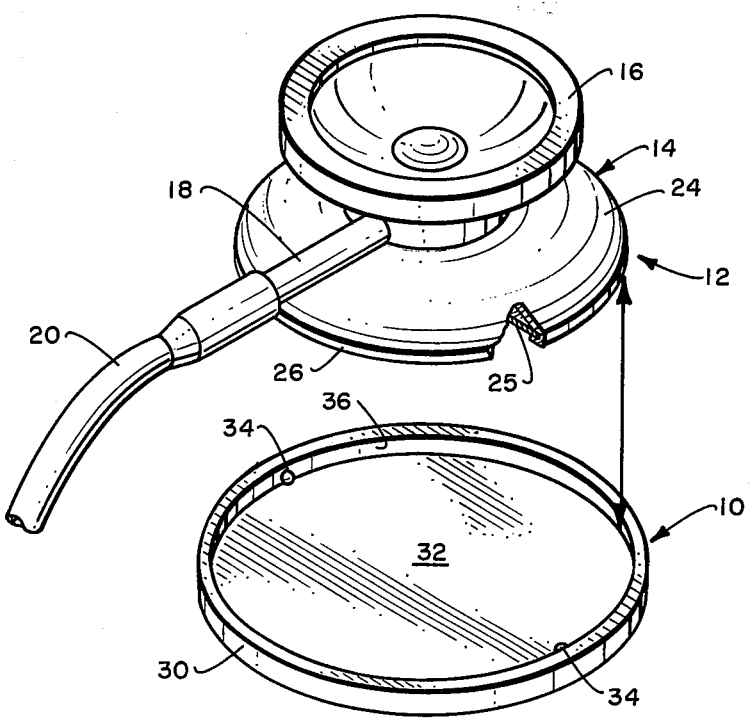
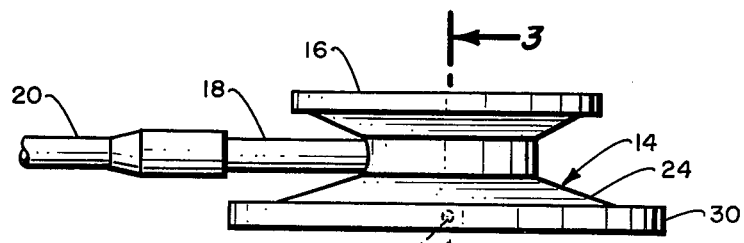
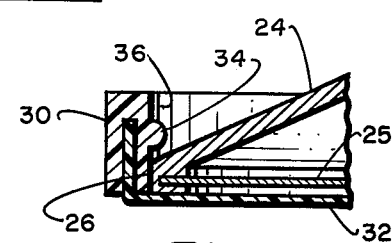
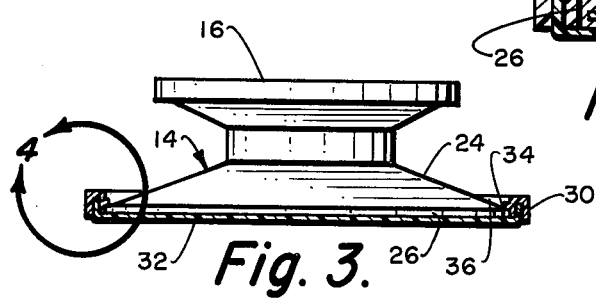
Fig. 1.
Fig. 2.
Fig. 3.
Fig. 4.

DIAPHRAGM COVER FOR A STETHOSCOPE

DESCRIPTION

1. Technical Field

The present invention relates to an attachment for a medical stethoscope and, more particularly, to a disposable cover for the diaphragm portion of the head of a stethoscope in order to maintain hygienic conditions and to prevent contamination of the patient's skin by the stethoscope, and vice-versa, thus eliminating the need to sterilize the head between examinations.

2. Background Art

The stethoscope is a clinical, diagnostic instrument for performing mediate auscultation. By means of this instrument the respiratory, cardiac, pleural, arterial, venus, uterine, fetal, intestinal and other sounds are conveyed to the ear of the observer. The most common stethoscope utilized is a binaural model including a transponder head acoustically connected to two ear pieces. A stethoscope does not amplify sound but it does filter extraneous noises and somewhat modifies the sound as it transmits it from the chest or other body portion to the ear pieces. Two types of acoustical pick-ups are required since there are different ranges of sound pitch emanating from the body.

Low-pitched sounds such as the murmur of mitral stenosis and fetal heart sounds are picked up by a bell-piece, usually in the form of a hollow cone with a rim of hard rubber or plastic as a base. This bellpiece head may be used separately or combined with the Bowles chest-piece which is in the form of a flat cup covered with a semi-rigid diaphragm of a synthetic resin such as Bakelite that serves as a filter to exclude low-pitch sounds so that the isolated high-pitch sounds appear to be amplified. The diaphragm transponder is used more frequently in practice to monitor high-pitch sounds from the heart and breath sounds from the lungs. Correct usage of the Bowles chestpiece requires that the entire surface of the diaphragm touch the skin and therefore the diaphragm is pressed tightly against the chest wall or other body portion being monitored. In contrast, the bellpiece should touch the chest wall lightly but completely. Heavy pressure with the bell stretches the underlying skin so that the skin becomes a diaphragm excluding low-pitch sounds.

The stethoscope is used quite frequently, especially during examination of patients in a doctor's office, in hospital clinics, emergency rooms or while conducting hospital rounds. Typically, during an examination, the stethoscope will be directly applied to the skin of the neck, chest, back or inguinal portions of the patients. Obviously, the diaphragm becomes soiled and contaminated during examination and will, in turn, contaminate the next patient's skin unless the stethoscope is sterilized between each examination.

In practice, medical personnel do not sterilize the stethoscope between examinations of different patients; especially during hospital rounds or busy situations. Even if sterilization is practiced, it is very hard to clean crevices and surfaces of stethoscope with alcohols or other conventional liquid disinfectants.

There are no devices on the market for maintaining hygienic condition of the skin contacting surfaces of the stethoscope head in order to prevent inter-patients contamination.

It is further to be recognized that the diaphragm portion of the head is used much more frequently and must be used by pressing the diaphragm firmly against skin and therefore has a larger surface area in contact with the skin and more probability of being contaminated. The bell portion is used much less frequently and is only in contact in a light pressure manner with a narrow circumfential end section of the bell device. Further, the bell is generally used for thorough examination of the heart, when ample time is available for examination and cleaning of the stethoscope, should the physician want to do the latter.

U.S. Pat. No. 3,255,841 to Hasbrouck discloses a plastic or rubber disposable cover for the bell portion of a stethoscope to maintain the bell aseptic from patient to patient. However, the cover is form-fitting and includes an inner dome having a central opening to permit sound transmission. Therefore, this would not allow adequate sound transmission or collection from a diaphragm head nor would it prevent contamination of the diaphragm because of the central perforation. It must be recognized that any cover for a stethoscope transponder must not interfere with sound transmission.

U.S. Pat. No. 3,867,925 to Ersek interposes a thin membrane between the diaphragm and the skin. However, the membrane is a ring shaped adhesive film which would interfere with firm application of the diaphragm surface to the skin, would deposit an adhesive residue on the diaphragm and would not prevent contamination of the patients' skin by the stethoscope or vice-versa.

BRIEF SUMMARY OF THE INVENTION

It has now been discovered in accordance with the invention that the surface of the diaphragm can be used without direct contact with the patient's skin and that it can be maintained in hygienic condition without significantly interfering with the collection and transmission of sound, thus eliminating contamination. This is accomplished in accordance with the invention by provision of a removable cover for the diaphragmatic surface. However, the characteristics of the material of the cover and the manner in which it is mounted on the diaphragm are critical to obtaining adequate sound transmission and the capability of sterilization and reuse of the cover, if desired.

It is not possible to maintain the stethoscope head aseptic (i.e, free of micro-organisms) since it can be readily contaminated by the air, fingers or surrounding objects (e.g, table . . . ) The cover of the invention:

1. Prevents gross soiling of the head by skin debris or dirt;
2. Prevents contamination of the patient's skin by the head, if soiled;
3. Thus, ultimately eliminating the transmission of (particles of) dirt and of micro-organisms from one patient to another.

The cover avoids direct contact between the surface of the diaphragm and the skin of the patient during examination, thereby preventing contamination of the stethoscope head by the patient's skin and the next patient's skin by the stethoscope head. The used, potentially infected cover is removed and a new cover is installed before examination of the next patient. There is no need to clean nor disinfect the stethoscope head between examination of successive patients.

The disposable cover as designed in accordance with the invention does not appreciably interfere with the collection and transmission of sound by the stethoscope.

Though the cover may be disposable, it can be constructed of material capable of sterilization by heat or disinfection by liquid sterilants such as ethyl alcohol, isopropyl alcohol, sterilant gas or ethylene oxide. Therefore, the cover may be used and reused many times before disposal. A cover can also be installed on a previously soiled stethoscope head so that the diaphragmatic surface is isolated from the patient's skin. This procedure is much quicker and more convenient than cleaning or disinfecting the stethoscope. The use of diaphragm covers is especially needed in the case of a physician conducting successive examinations during hospital rounds or in busy office or emergency room situations. Doctors are supposed to wash their hands between examinations though their hands may not directly contact the patients. However, they do not disinfect the stethoscope head which directly contacts the patient. Another advantage of the diaphragm cover of the invention is that it thermally insulates the surface of the stethoscope, consequently avoiding application of a cold metallic object to the surface of the patient's skin.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is an exploded, perspective view of the combination of a Littman stethoscope head and the disposable cover of the invention;

FIG. 2 is a side view in elevation of the cover of the invention shown attached to the diaphragm portion of a Littman head;

FIG. 3 is a partial cross-sectional view taken on line 3—3 of FIG. 2; and

FIG. 4 is an enlarged cross-sectional view taken from FIG. 3.

DETAILED DESCRIPTION OF THE INVENTION

Referring now to FIG. 1, the disposable cover 10 is shown in relation to a Littman stethoscope head 12. The diaphragm cover 10 can be used with any stethoscope diaphragm provided it is structurally figured to closely fit the diameter of the diaphragm; though most of the stethoscopes in use today utilize the basic Littman design.

The head 12 comprises a diaphragm portion 14, a bell portion 16 and a tubular outlet member 18 containing an air column. A flexible hose 20 connects the outlet 18 to a hinge which in turn is attached to the binaural earpiece members, not shown. The diaphragm portion 14 is formed of a flat cup 24 on which is mounted a semi-rigid diaphragm 25, held in place by a circular ring 26.

Referring now to FIGS. 2 and 3, the disposable cover 10 is formed of a fairly rigid rim member 30, having a sheet 32 of flexible elastomar stretched over the front surface of the rim and attached thereto. The cover further contains at least one, preferably at least two, locking members 34 mounted on the inner edge 36 of the rim 30.

The locking members 34 can be arcuate, flat, cylindrical or can be hemispherical in shape. The inner diameter, measured from the innermost projection of the tabs, is narrower than the diameter of the circular ring 26 surrounding cup 24 so that the tab or tabs 34 snap over the outer edge of the ring 26 and lock onto the slanting surface of the ring 26. The locking fit should not be too tight or sound dampening can occur. A loose fit of the cover suffices. The hemispherical-shaped tabs are preferred since they provide a tapering surface in both the insertion and removal directions. A tolerance of about 1 mm between the inner surface of the rim and the outer diameter of the ring 26 permits easy insertion of the cover over the ring 26 while the tabs insure retention of the cover. This tolerance also provides a sufficiently loose fit to avoid sound dampening. Sound dampening can also occur if the tabs are too close to the membrane and lock rigidly onto the ring and/or stretch the membrane.

The rim should be formed of fairly rigid material so the cover will more reliably lock onto the ring. Though the rim can be formed of an elastomer, plastic resin, metal, wood, etc., it is preferably formed of a fairly stiff resin such as an acrylic, suitably a polymethylmethacrylate such as Plexiglas. The rim need only have sufficient thickness to provide structural integrity, suitably from 0.1 to 0.5 cm in thickness. However, the cover sheet to be mounted on the rim should be fairly resilient or sound transmission is substantially affected. During pressing of the diaphragm onto a patient, a rigid, stiff cover sheet would act as a barrier, absorb the sound and transmit it to the rim. However, only an elastomeric sheet would stretch, deform and permit continuous contact between the diaphragm and the skin of the patient. The cover sheet should be as thin as possible, generally from 1 to 10 mils and should be absent of pinholes. A preferred material is latex rubber of the type utilized for surgical gloves. This material can be sterilized for repeated use by immersion in sterilizing liquid such as isopropyl alcohol.

A diaphragm cover for a particular Littman-type stethoscope was constructed. The device consisted of a rim formed of a circular band (thickness: 0.15 cm; height: 0.50 cm; inside diameter: 4.8 cm) made of Plexiglas to which a very thin (0.006") circle-shaped membrane made of rubber of the type used for surgical gloves and having a radius equal to the outer radius of the rim was attached to the rim. The inside diameter of said rim was made slightly larger (by about 1 mm) than the outside diameter of the diaphragmatic surface of the stethoscope head to allow easy insertion of the stethoscope head in the device. To ensure retention of the device on the stethoscope head, two small semi-circular flaps were provided on the inside surface of the rim near the opening. The exact dimensions and relative proportions of the device may vary depending on the stethoscope head for which the device is specifically made. The device described above was made to fit the regular combined "Littman" stethoscope for physicians. If necessary for certain stethoscope types, a small half-circular indentation can be made on the upper ridge of the circular band to allow room for the cylinder connecting the stethoscope head to the flexible tubes of the stethoscope.

The device has been tested in practice and is found to be convenient to insert and remove, does not interfere with sound transmission and collection, and is readily resterilized. Earlier prototypes manufactured with rigid membrane sheets were found to interfere with sound collection and transmission. Prototypes with resilient rims were not as convenient to use in practice. If a large supply of the covers is available, they could be sterilized as a batch and be stored and dispensed in a convenient place in an office examining room or hospital so that a continuous supply of sterile devices is available from a limited number of covers.

I claim:

1. In combination:

a stethoscope having a diaphragm portion in the form of a cup-shaped element receiving a flat diaphragm element;

a removable cover releasably attached at an end portion of the cup-shaped element comprising in combination;

a semi-rigid rim having a diameter slightly larger than said end portion;

a resilient, continuous, imperforate, flexible, and deformable sheet of sterilizable elastomer attached to the outer edge of the rim; and retaining means comprising a plurality of protrusions mounted on the inner surface of the rim engaging the outer edge of the end portion of the cup for releasably maintaining said cover on said diaphragm portion.

2. A cover according to claim 1 in which the elastomer is a natural rubber latex.

3. A cover according to claim 2 in which the rim is formed of an acrylic resin.

4. A cover according to claim 3 in which the acrylic is a polymethylmethacrylate.

5. A cover according to claim 1 in which the protrusions are hemispherical in shape.

* * * * *